Figure 1:
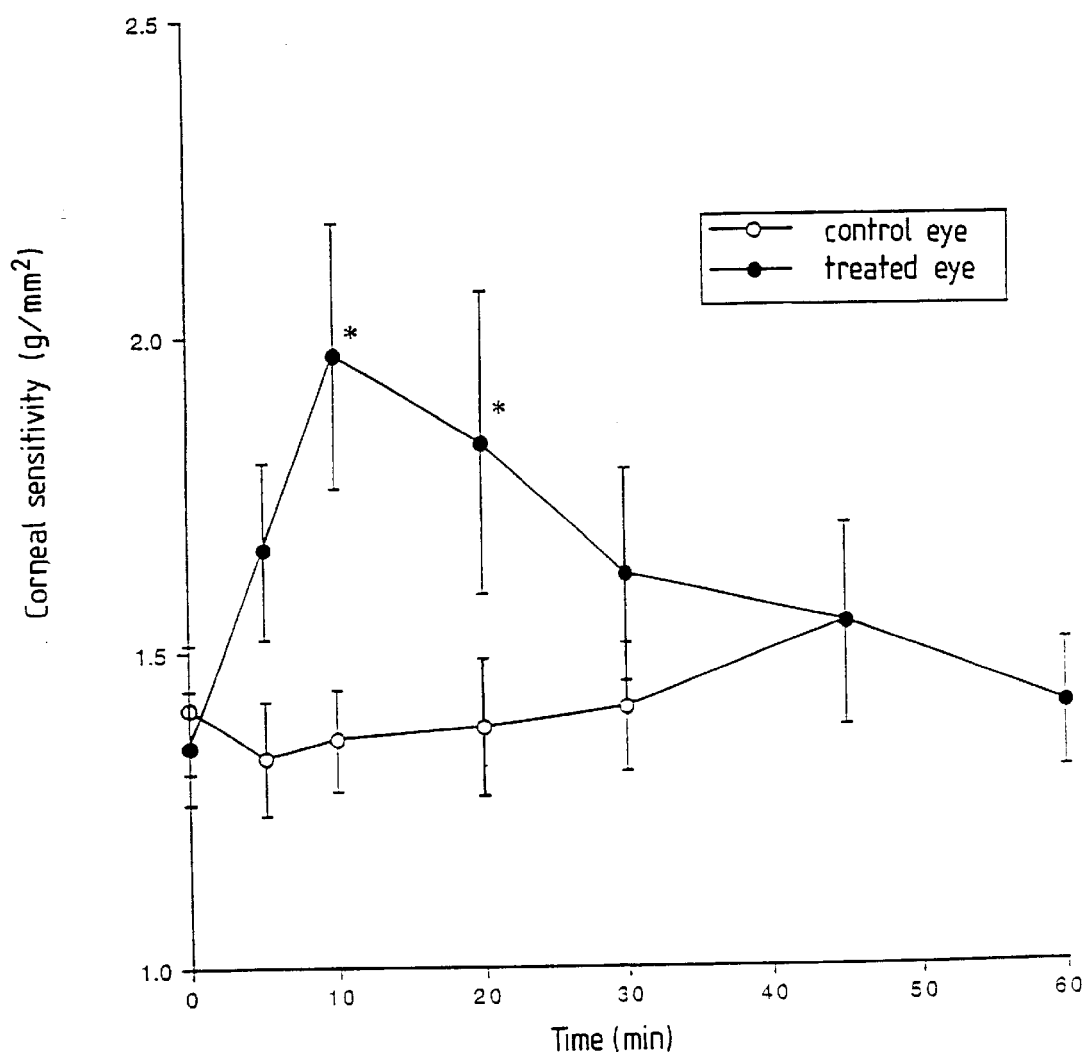

United States Patent [19]

Coquelet et al.

[11] Patent Number: 5,770,596
[45] Date of Patent: Jun. 23, 1998

[54] PHARMACEUTICAL COMPOSITIONS BASED ON MEQUITAZINE

[75] Inventors: Claude Coquelet, Saint Gely sur Fesc; Elisabeth Latour, Montpellier; Florence Maurin, Vailhauques, all of France

[73] Assignee: Laboratoire Chauvin S.A., Montpellier, France

[21] Appl. No.: 757,969

[22] Filed: Dec. 5, 1996

[30]  Foreign Application Priority Data

Dec. 6, 1995 [FR] France ................................. 95 14425

[51] Int. Cl.$^6$ .......................... A61K 31/54; A61K 31/70
[52] U.S. Cl. ...................... 514/225.2; 514/58; 514/912
[58] Field of Search .................................. 514/225.2, 58, 514/912

[56]  References Cited

U.S. PATENT DOCUMENTS 5,192,780  3/1993  York et al. .............................. 514/357

FOREIGN PATENT DOCUMENTS

A02003610  6/1988  Japan .

*Primary Examiner*—Phyllis G. Spivack
*Attorney, Agent, or Firm*—Jacobson, Price, Holman & Stern, PLLC

[57]  ABSTRACT

The subject of this invention is a ready-for-use collyrium intended for the treatment of ocular allergies, comprising, in aqueous solution, mequitazine and a β- or a γ-cyclodextrin optionally etherified by $C_1$–$C_4$ alkyl or $C_1$–$C_4$ hydroxyalkyl groups, the said cyclodextrin being present in at least a molar ratio of at least one in relation to mequitazine.

9 Claims, 2 Drawing Sheets

PHARMACEUTICAL COMPOSITIONS BASED ON MEQUITAZINE

The present invention relates to pharmaceutical compositions based on mequitazine.

Mequitazine is a derivative of phenothiazine (10-(3-quinuclidinylmethyl)phenothiazine) which has been described as an H1 antihistaminic and which is used orally for the treatment of various allergic manifestations, including at the ocular level.

However, mequitazine has been described as having an anesthetic activity slightly superior to that of lidocaine (HoJo et al., Folia Pharmacologica Japonica 78 (5), 403, 1981).

Moreover, in JP-A-02 003 610, a syrup has been described which contains mequitazine (0.03 to 0.05%), 40 to 60% (w/v) of a sugar such as sorbitol or mannitol and a β- or γ-cyclodextrin as solubilizer.

The aim of the present invention is to provide a composition intended for the local treatment of ocular allergies which exhibits excellent tolerance and which in particular does not induce locally an anesthetic effect, which effect must be avoided in a local treatment because it causes a decrease in corneal sensitivity and therefore risks of damage of the cornea following uncontrolled rubbing by the patient.

The present invention relates to a ready-for-use collyrium intended for the treatment of ocular allergies, comprising, in aqueous solution, mequitazine and a β- or a γ-cyclodextrin optionally etherified by $C_1$–$C_4$ alkyl or $C_1$–$C_4$ hydroxyalkyl groups, the said cyclodextrin being present in a molar ratio of at least one in relation to mequitazine.

The optionally etherified β- and γ-cyclodextrins are compounds which are widely known and commercially available. They are cyclic structures consisting respectively of 7 or 8 anhydroglucose units. Each of the glucose units contains 3 hydroxyl groups which may be in part etherified by $C_1$–$C_4$ alkyl or $C_1$–$C_4$ hydroxyalkyl groups. The degree of substitution by the anhydroglucose unit varies generally from 0.05 to 2, especially from 0. 2 to 2.

In the present invention, hydroxypropyl-β-cyclodextrin is most particularly preferred, but there may also be used in particular hydroxyethyl-β-cyclodextrin, hydroxybutyl-β-cyclodextrin and hydroxypropyl-γ-cyclodextrin.

The hydroxypropyl-β-cyclodextrin advantageously has an etherification value of 0.4.

The collyrium according to the present invention advantageously comprises from 0.01 to 0.5% by weight of mequitazine and especially 0.05% by weight of mequitazine.

The hydroxypropyl-β-cyclodextrin is advantageously used in a hydroxypropyl-β-cyclodextrin/mequitazine molar ratio of at least 4. A preferred collyrium contains 0.05% by weight of mequitazine and 1% by weight of hydroxypropyl-β-cyclodextrin.

The collyrium according to the invention may contain, in addition to mequitazine, cyclodextrin and water, customary adjuvants for a collyrium, namely preservatives, buffers and/or agents for adjusting the pH and isotonizing agents such as sorbitol, mannitol or glucose. These isotonizing agents may be present in proportions of 0 to 6% by weight.

An example of preparation of a collyrium according to the invention will be given below.

EXAMPLE 1

A ready-for-use collyrium having the following composition is prepared:

| | |
|---|---|
| Mequitazine: | 0.05 g |
| Benzalkonium chloride (solution for ophthalmic use) | 0.01 g |
| Sodium edetate: | 0.05 g |
| Hydroxypropyl-β-cyclodextrin*: | 1.00 g |
| Boric acid: | 1.50 g |
| Arginine: | 0.46 g |
| Sorbitol 70 % crystallizable: | 1.70 g |
| Purified water qs: | 100.00 ml |
| pH: | 6.00 |

*Product marketed by Janssen under the trademark Encapsin HPB having an average molecular mass of 1300, substitutions at positions 1 and 4 with an average degree of substitution of 0.4.

The collyrium is prepared by dissolving in water sodium edetate, boric acid and then hydroxypropylcyclodextrin.

Next, the mequitazine is added, then the sorbitol, the arginine in order to adjust the pH to 6 and then the benzalkonium chloride.

Results of the pharmacological studies demonstrating the properties of the collyrium according to the invention will be given below.

1. Study of the antihistaminic activity of collyria containing mequitazine with or without hydroxy-propyl-β-cyclodextrin in a model of ocular allergy induced with histamine in guinea pigs.

The experiments were carried out on male Hartley guinea pigs, of an average weight of 300 g, obtained from the breeding centre Charles River France (Saint Aubin les Elbeuf—76140 CLEON), acclimatized for five days in an animal house before the beginning of the study.

The animals, anesthetized with ketamine (40 mg/kg intramuscularly) and with xylazine (5 mg/kg subcutaneously) were shaved in the superosternal region and a 3 cm incision was made in order to expose a jugular vein.

A 4% Evans Blue solution in physiological saline was injected in an amount of 0.5 ml/kg (20 mg/kg) into the jugular with the aid of a syringe equipped with a 26-gauge needle. A pressure applied for a few seconds to the vein allows the formation of a clot and avoids any haemorrhage.

One minute after injection of the Evans Blue solution, conjunctival edema was induced in both eyes by instillation of 10 µl of a solution containing 30 µg of histamine base in physiological saline.

Fifteen minutes later, the animal was sacrificed by intracardiac injection of pentobarbital, and the eyelids and the eyeball were removed immediately.

These samples (after opening the eyeball and removing the crystalline lens) were extracted, for each eye, separately with 10 ml of an acetone/sodium sulphate 0.5% (7v/3v) mixture overnight with gentle stirring. After centrifugation at 1800×g for 15 minutes, the Evans Blue concentration in the extract was determined by spectrophotometry at 620 nm, in comparison with a calibration curve.

The experiments were carried out on 54 animals divided into 9 batches of six animals, treated with the following different collyria:

physiological saline (control batch), collyria containing mequitazine at different concentrations, without hydroxypropyl-β-cyclodextrin.

|  | 0.1% | 0.05% | 0.005% | 0.0005% |
|---|---|---|---|---|
| Mequitazine | 0.10 g | 0.05 g | 0.005 g | 0.0005 g |
| Sodium edetate | 0.05 g | 0.05 g | 0.05 g | 0.05 g |
| Arginine | 0.46 g | 0.46 g | 0.46 g | 0.46 g |
| Sorbitol 70% crystallisable | 1.70 g | 1.70 g | 1.70 g | 1.70 g |
| Boric acid | 1.50 g | 1.50 g | 1.50 g | 1.50 g |
| Benzalkonium chloride solution for ophthalmic use | 0.01 g | 0.01 g | 0.01 g | 0.01 g |
| Purified water qs | 100 ml | 100 ml | 100 ml | 100 ml |
| pH |  | 6.0 ± 0.1 |  |  | collyria containing mequitazine at different concentrations with hydroxypropyl-β-cyclodextrin

|  | 0.1% | 0.05% | 0.005% | 0.0005% |
|---|---|---|---|---|
| Mequitazine | 0.10 g | 0.05 g | 0.005 g | 0.0005 g |
| Sodium edetate | 0.05 g | 0.05 g | 0.05 g | 0.05 g |
| Hydroxypropyl-β-cyclodextrin | 2.00 g | 1.00 g | 0.10 g | 0.01 g. |
| Arginine | 0.46 g | 0.46 g | 0.46 g | 0.46 g |
| Sorbitol 70 % crystallisable | 1.70 g | 1.70 g | 1.70 g | 1.70 g |
| Boric acid | 1.50 g | 1.50 g | 1.50 g | 1.50 g |
| Benzalkonium chloride solution for ophthalmic use | 0.01 g | 0.01 g | 0.01 g | 0.01 g |
| Purified water qs | 100 ml | 100 ml | 100 ml | 100 ml |
| pH |  | 6.0 ± 0.1 |  |  |

The hydroxypropyl-β-cyclodextrin/mequitazine weight ratio was kept constant.

One hour before the induction of conjunctival oedema, the animals were treated in both eyes by instillation of 10 μl of the test collyrium.

The results, expressed in the form of a mean ± standard deviation, are summarized in the following table:

| Collyrium | Vascular leakage (μg of Evans Blue/eye) | Inhibition % |
|---|---|---|
| Physiological saline | 31.28 ± 11.42 | — |
| Mecuitazine 0.1% | 4.37 ± 4.44 | 86 |
| Mequitazine 0.1% (HPβCD) | 4.16 ± 4.72 | 87 |
| Mequitazine 0.05% | 2.73 ± 3.01 | 91 |
| Mecuitazine 0.05% (HPβCD) | 3.12 ± 3.07 | 90 |
| Mecuitazine 0.005% | 7.73 ± 6.83 | 75 |
| Mequitazine 0.005% (HPβCD) | 6.97 ± 5.43 | 78 |
| Mequitazine 0.0005% | 10.07 ± 5.48 | 68 |
| Mequitazine 0.0005% (HPβCD) | 9.05 ± 3.35 | 71 |

These results show that mequitazine administered in the form of a collyrium inhibits the increase in the vascular permeability induced by histamine and that the addition of hydroxypropyl-β-cyclodextrin to these collyria, in a weight ratio of 20 to 1, does not modify the antihistaminic activity of mequitazine.

2. Effect of mequitazine in the form of a collyrium in the presence or in the absence of hydroxypropyl-β-cyclodextrin on the corneal sensitivity in rabbits.

The objective of this study was to compare two mequitazine formulations in the form of a collyrium at 0.2% in order to verify if the presence of hydroxypropyl-β-cyclodextrin in the excipient was capable of modifying the local anesthetic activity of this active ingredient.

The experiments were carried out on Now Zealand albino male rabbits weighing from 3 kg to 3.5 kg, obtained from the breeding farm Charles River France (St Aubin lee Elbeuf—76410 CLEON), acclimatized for a minimum of 5 days in an animal house (temperature: 19±2° C.; relative humidity: 55±10%; lighting: 12 hours of artificial light—12 hours of night).

The following compositions were used for the tests:

collyrium containing 0.2% mequitazine without hydroxypropyl-β-cyclodextrin

|  | Mequitazine | Placebo |
|---|---|---|
| Mequitazine | 0.20 g | — |
| Sodium edetate | 0.05 g | 0.05 g |
| Arginine | qs pH 6 | 0.07 g |
| Sorbitol 70% crystallisable | 6.79 g | 6.79 g |
| Hydrochloric acid | qs dissolution | qs pH 6 |
| Benzalkonium chloride solution for ophthalmic use | 0.01 g | 0.01 g |
| Purified water qs | 100.00 ml | 100.00 ml |
| pH | 6.00 | 6.00 | collyrium containing 0.2% mequitazine with hydroxypropyl-β-cyclodextrin (Encapsin® HPB)

|  | Mequitazine | Placebo |
|---|---|---|
| Mequitazine | 0.20 g | — |
| Sodium edetate | 0.05 g | 0.05 g |
| Hydroxypropyl-β-cyclodextrin | 4.00 g | 4.00 g |
| Arginine | qs pH 6 | 0.07 g |
| Sorbital 70% crystallisable | 5.83 g | 5.83 g |
| Hydrochloric acid | qs dissolution | qs pH 6 |
| Benzalkonium chloride solution for ophthalmic use | 0.01 g | 0.01 g |
| Purified water qs | 100.00 ml | 100.00 ml |
| pH | 6.00 | 6.00 |

The corneal sensitivity was measured at the centre of the cornea with the Cochet and Bonnet aesthesiometer (Luneau Ophtalmologie, Chartres).

The animals were selected beforehand according to their response threshold (pressure of less than or equal to 2.40 g/mm$^2$) and divided into two batches of eight animals.

On the day of the experiment, the sensitivity was measured three times in both eyes at 20 minute intervals before any treatment (time 0). The animals were treated in one eye with an instillation of 25 μl of the collyrium containing mequitazine at 0.2%, formulated in the presence or in the absence of hydroxypropyl-β-cyclo-dextrin; the controlateral eye received 25 μl of the corresponding placebo. The corneal sensitivity was determined in both eyes 5, 10, 20, 30, 45 and 60 minutes after instillation.

The corneal sensitivity is expressed in the form of the pressure exerted (in g/mm$^2$); an increase in pressure corresponds to a reduction in the corneal sensitivity. The results are expressed in the form of a mean ± standard error.

A factorial analysis of variance was used followed by the Newman-Keuls multiple comparisons test in order to determine the significance level of the difference between the means; this difference is considered to be significant when p is less than 0.05 (*).

Figure 2:
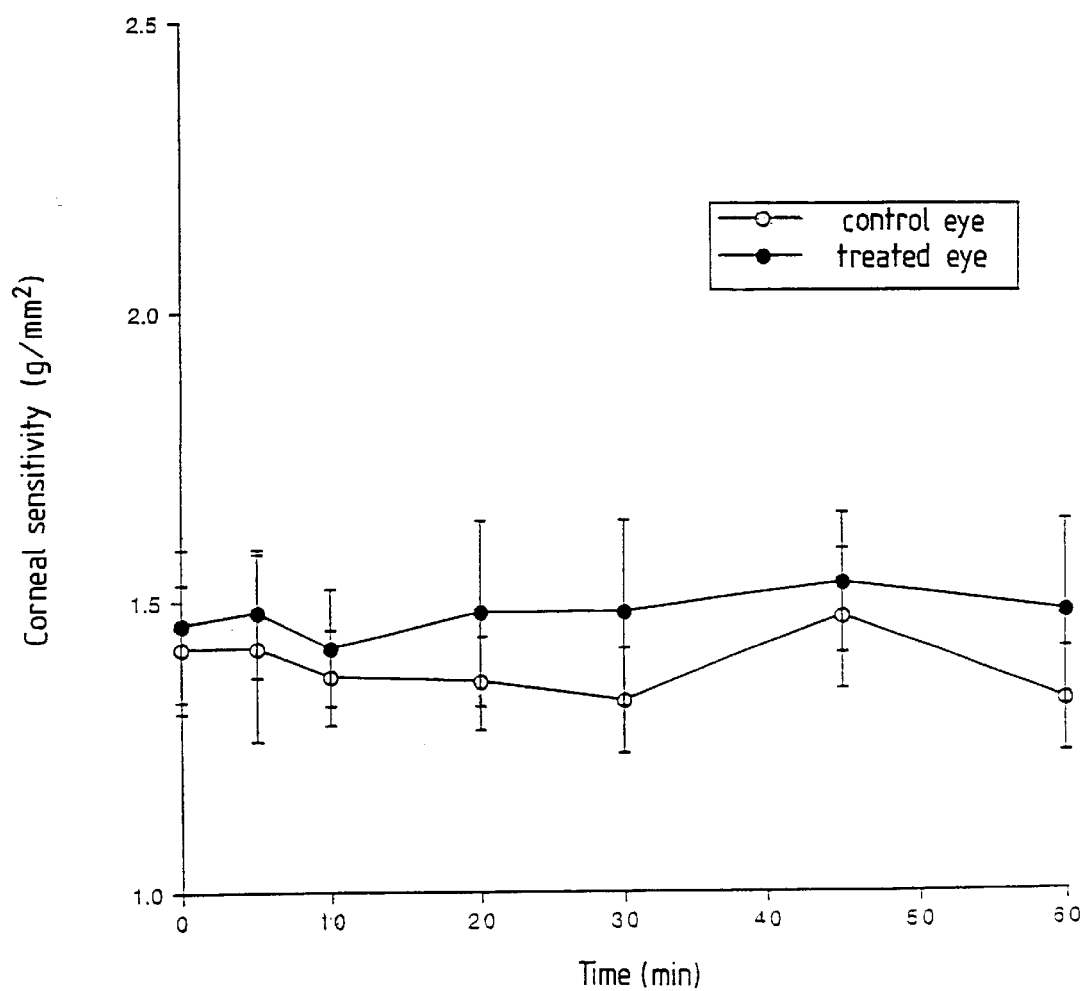

The results obtained with a collyrium without HPβPCD and with HPβPCD are shown in FIGS. 1 and 2 respectively.

Mequitazine in a collyrium at 0.2% formulated without the addition of hydroxypropyl-β-cyclodextrin causes a significant decrease in the corneal sensitivity 10 and 20 minutes after administration of a drop, compared with the controlateral eyes treated with the placebo (FIG. 1).

On the other hand, when mequitazine is administered at the same concentration in the presence of hydroxypropyl-β-cyclodextrin, no significant corneal hypoaesthesia is observed (FIG. 2).

The addition of hydroxypropyl-β-cyclodextrin in the excipient of the collyrium to mequitazine therefore causes a disappearance of the ocular anesthetic effects observed after instillation of this collyrium.

In the light of the study 1 on the antihistaminic effect and of the study 2 on the anaesthetic effect, it appears that, surprisingly, by virtue of the presence of hydroxypropyl-β-cyclodextrin, the anesthetic effect is suppressed whereas the antihistaminic effect is not affected.

We claim:

1. Ready-for-use collyrium intended for the treatment of ocular allergies, comprising, in aqueous solution, mequitazine and a β- or a γ-cyclodextrin optionally etherified by $C_1$–$C_4$ alkyl or $C_1$–$C_4$ hydroxyalkyl groups, the said cyclodextrin being present in a molar ratio of at least one in relation to mequitazine.

2. Collyrium according to claim 1, in which the cyclodextrin is hydroxypropyl-β-cyclodextrin.

3. Collyrium according to claim 2, in which the hydroxypropyl-β-cyclodextrin has a degree of substitution with the hydroxypropyl groups of 0.4.

4. Collyrium according to claim 1, comprising from 0.01 to 0.5% by weight of mequitazine.

5. Collyrium according to claim 2, in which the hydroxypropyl-β-cyclodextrin is present in a molar ratio of at least 4 in relation to mequitazine.

6. Collyrium according to claim 1 comprising 0.05% by weight of mequitazine.

7. Collyrium according to claim 6, comprising 1% by weight of hydroxypropyl-β-cyclodextrin.

8. Collyrium according to claim 1, comprising from 0 to 6% by weight of an isotonizing agent.

9. Process for the treatment of ocular allergies which comprises administering in the eye of a patient in need thereof a ready-for-use collyrium comprising, in aqueous solution, mequitazine and a β- or a γ-cyclodextrin optionally etherified by $C_1$–$C_4$ alkyl or $C_1$–$C_4$ hydroxyalkyl groups, the said cyclodextrin being present in a molar ratio of at least one in relation to mequitazine, said process having no local anesthesic effect.

* * * * *